US00RE47268E

(19) United States
(12) Reissued Patent
Roa-Espinosa

(10) Patent Number: US RE47,268 E
(45) Date of Reissued Patent: Mar. 5, 2019

(54) SEPARATION OF BIOCOMPONENTS FROM DDGS

(71) Applicant: Aicardo Roa-Espinosa, Madison, WI (US)

(72) Inventor: Aicardo Roa-Espinosa, Madison, WI (US)

(21) Appl. No.: 15/273,133

(22) Filed: Nov. 16, 2016

Related U.S. Patent Documents

Reissue of:

(64) Patent No.: 9,051,538
Issued: Jun. 9, 2015
Appl. No.: 14/518,310
Filed: Oct. 20, 2014

U.S. Applications:

(63) Continuation-in-part of application No. 14/190,332, filed on Feb. 26, 2014, now abandoned.

(51) Int. Cl.

| | |
|---|---|
| ***A23J 1/00*** | (2006.01) |
| ***B03D 1/01*** | (2006.01) |
| ***B03D 1/02*** | (2006.01) |
| ***B03D 1/10*** | (2006.01) |
| ***C02F 1/24*** | (2006.01) |
| ***C02F 1/52*** | (2006.01) |
| ***C02F 3/10*** | (2006.01) |
| ***C02F 9/00*** | (2006.01) |
| ***C07K 1/30*** | (2006.01) |
| ***C08B 1/00*** | (2006.01) |
| ***C12F 3/10*** | (2006.01) |
| ***A23K 10/38*** | (2016.01) |
| ***B30B 13/00*** | (2006.01) |

(Continued)

(52) U.S. Cl.
CPC ..... *C12F 3/10* (2013.01); *A23J 1/005* (2013.01); *A23K 10/38* (2016.05); *B03D 1/01* (2013.01); *B03D 1/02* (2013.01); *B03D 1/10* (2013.01); *B30B 13/00* (2013.01); *C02F 1/24* (2013.01); *C02F 1/5272* (2013.01); *C02F 3/10* (2013.01); *C02F 9/00* (2013.01); *C08B 1/00* (2013.01); *C11B 13/00* (2013.01); *C02F 2103/32* (2013.01); *C07K 1/30* (2013.01); *C08L 89/00* (2013.01); *Y02P 60/873* (2015.11); *Y02W 30/74* (2015.05)

(58) Field of Classification Search
CPC .. C12F 3/10; C02F 1/5272; C02F 3/10; C02F 9/00; C02F 2103/32; C02F 1/24; C11B 13/00; B03D 1/02; B03D 1/01; B03D 1/10; C07K 1/30; C08B 1/00; B30B 13/00
See application file for complete search history.

(56) References Cited

U.S. PATENT DOCUMENTS 7,014,774 B2 * 3/2006 Yamada et al. ..... 210/708
7,857,872 B2 * 12/2010 Krasutsky et al. ..... 44/605

(Continued)

*Primary Examiner* — Elizabeth L McKane
(74) *Attorney, Agent, or Firm* — Steven H Greenfield; Greenfield Invention and Patent Consulting, Inc.

(57) ABSTRACT

A multi stage process for the separation of bio-components from a waste stream containing Dried Distillers Grains with Solubles is disclosed. Targeted polymers are added to the source and separated streams prior to passing the streams through separation equipment including a rotary screen, a press, and a dissolved air floatation in which the waste stream is separated into a stream containing predominantly protein, a stream containing predominantly oil, a stream containing predominantly water and a stream that contains predominantly fibers.

22 Claims, 2 Drawing Sheets

(51) Int. Cl.

| | |
|---|---|
| ***C08L 89/00*** | (2006.01) |
| ***C11B 13/00*** | (2006.01) |
| ***C02F 103/32*** | (2006.01) |

(56) References Cited

U.S. PATENT DOCUMENTS

| | | | | |
|---|---|---|---|---|
| 2006/0006116 | A1* | 1/2006 | Scheimann et al. | 210/728 |
| 2007/0172913 | A1* | 7/2007 | Hughes | C02F 1/56 435/41 |
| 2008/0026101 | A1* | 1/2008 | Nickel et al. | 426/52 |
| 2010/0178675 | A1* | 7/2010 | Lawton et al. | 435/71.1 |
| 2010/0224711 | A1* | 9/2010 | Kreisler et al. | 241/21 |
| 2011/0079219 | A1* | 4/2011 | McDonald et al. | 127/1 |
| 2012/0045545 | A1* | 2/2012 | Mielgo et al. | 426/31 |
| 2012/0125859 | A1* | 5/2012 | Collins et al. | B01D 17/0217 210/708 |
| 2013/0164795 | A1* | 6/2013 | Lowe et al. | 435/134 |

* cited by examiner

SEPARATION OF BIOCOMPONENTS FROM DDGS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application is a continuation in part application claiming priority from non-provisional application Ser. No. 14/190,332 filed on Feb. 26, 2014.

FIELD OF THE INVENTION

The present invention relates generally to a process of recovering useful materials from waste sources that include Dried Distillers Grains with Solubles also known by the acronym DDGS, waste materials from ethanol production and animal feed waste.

BACKGROUND OF THE INVENTION

Thin stillage and distillers' grains are byproducts remaining after alcohol distillation from a fermented cereal grain mash. Both byproducts are used as energy and protein sources for ruminants. There are two main sources of these byproducts. The traditional sources were from brewers. However, more recently, ethanol plants such as corn, sugar cane, cassaya and potatoes have become a growing source.

DDGS contain valuable bio-materials mainly fibers, oil and protein. The oil in DDGS could be used either as cooking oil or as a biofuel. The main protein in corn is Zein which has been used in the manufacture of a wide variety of commercial products, including coatings for paper cups, soda bottle cap linings, clothing fabric, buttons, adhesives, coatings and binders, recently this protein has been used as a coating for candy, nuts, fruit, pills, and other encapsulated foods and drugs. Additionally Zein can be further processed into resins and other bioplastic polymers. Fibers may be used as raw materials in the production of lignocellulosic ethanol. Residue materials from ethanol production contain fibers from which ethanol has been extracted. However, only about 50-70% of the ethanol in these materials is typically extracted leaving substantial portion of ethanol that is available for further extraction. Tables 1 and 2 provide a typical content breakdown of the various materials in DDGS.

TABLE 1

Cellulosic biomass compositional analysis of DDGS.

| | Average |
|---|---|
| Dry matter | 88.8 |
| Water extractives | 24.7 |
| Ether extractives | 11.6 |
| Crude protein | 24.9 |
| Glucan (total) | 21.2 |
| Cellulose | 16 |
| Starch | 5.2 |
| Xylan and Arabinan | 13.5 |
| Xylan | 8.2 |
| Arab Man | 5.3 |
| Ash | 4.5 |
| Total dry matter | 100.4 |

TABLE 2

Nutritional Compositional analysis of DDGS.
Nutritional Compositional analysis

| | |
|---|---|
| Dry matter | 88.9 |
| Crude at | 14.5 |
| Carbohydrates | 53.5 |
| Ash | 4.7 |
| Total | 100 |

It would therefore be desirable to provide a process to separate these materials in order to maximize their uses.

SUMMARY OF THE PRESENT INVENTION

In an aspect of the present invention, a multi-stage substantially continuous process for separating a source stream said source stream intermixedly containing fibers, water, protein and oil, said process being configured for separating the source stream into streams each containing predominantly one component, said source stream containing dried distillers grains with solubles, said process comprises the stages of: providing a source stream comprising dried distillers grain with solubles, said dried distillers grain stream containing water, oil, protein and fibers; separating said source stream into a second stream and a third stream, said second stream containing predominantly fibers, said third stream containing predominantly a mixture of oil, protein and water, said separating being accomplished through the treatment of the first stream with; separating a fourth stream and a fifth stream from said third stream, said fourth stream containing predominantly water and said fifth stream containing predominantly oil and protein; and separating from the fifth stream a stream containing predominantly oil and a stream comprising predominantly protein through the steps of drying, size reduction, and pressing out the oil.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention.

The main components of Raw Dried Distillers Grains with Solubles (DDGS) include water in the range of between about 70% to about 95%, but could also be higher or lower depending on the source.

It is desirable that the water content of the source DDGS stream be consistent in order for the process to be stable. Therefore, water is added as needed to ensure that the solids level in the DDGS entering the process does not exceed 30%.

The process consists of mechanical separation steps aided by polymeric additions to separate the DDGS into four streams each containing predominantly one component: fibers, water, oil and protein.

Figure 1:
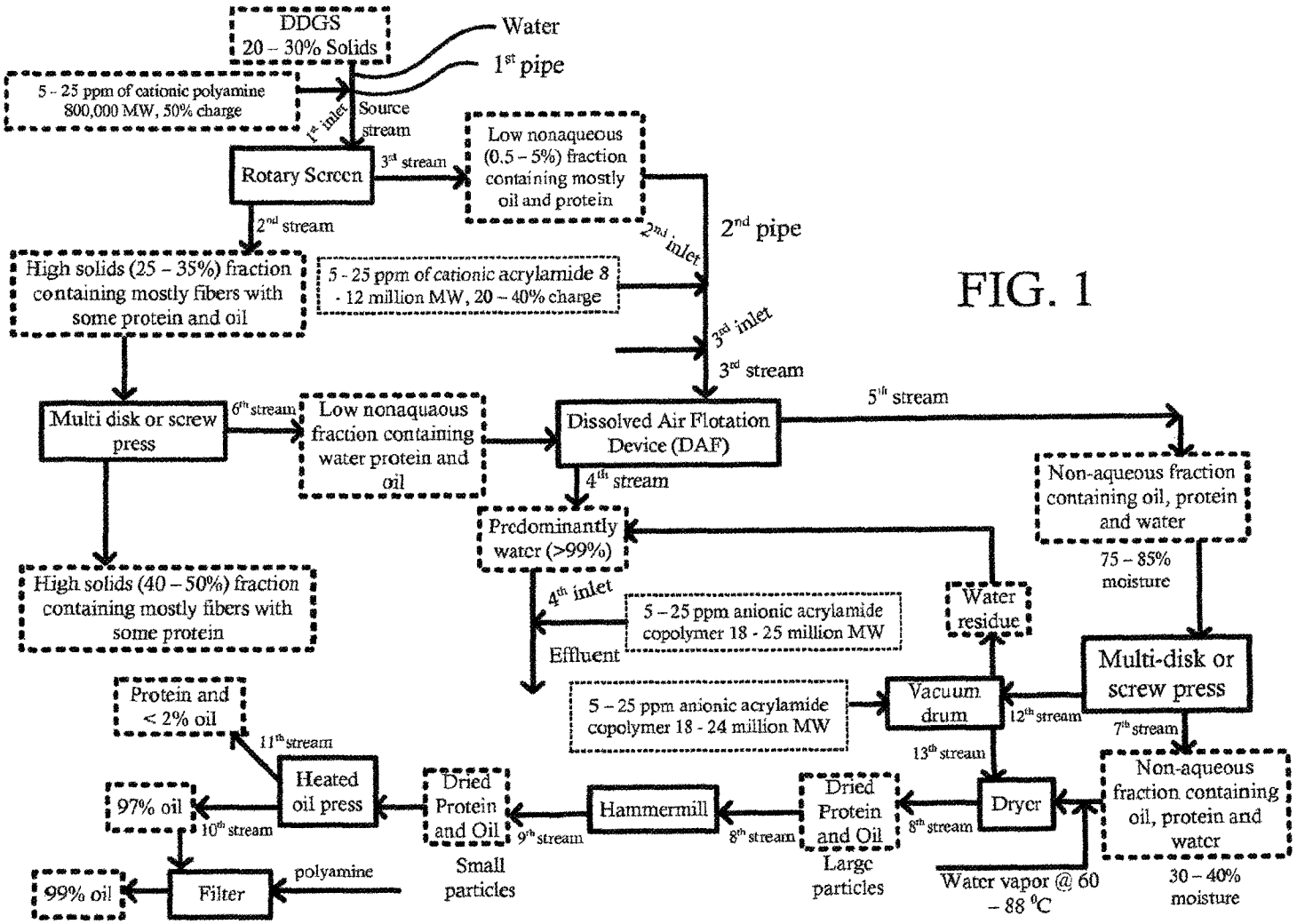
FIG. 1 is a flow chart schematic of the process according to an embodiment of the present invention.
Figure 2:
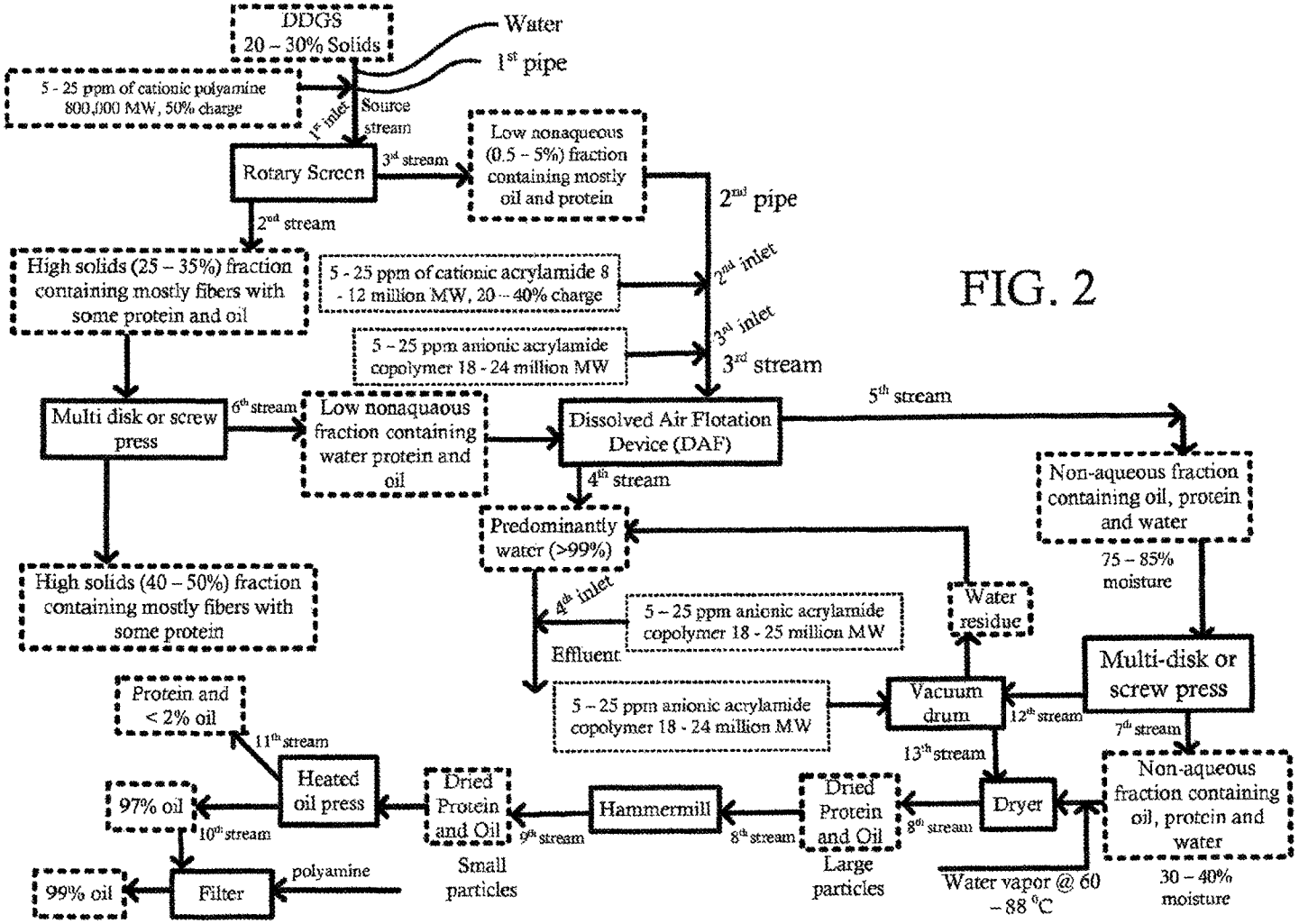
FIG. 2 is a flow chart schematic of the process according to another embodiment of the present invention.

In the first step, the DDGS source stream is introduced into a rotary screen through a 1" pipe. Between 5-25 ppm of a cationic polyamine having a 50% charge and a MW of about 800,000 are added to the pipe. This helps precipitate a stream that contains water and non-aqueous matter, predominantly fibers ranging in length from some 0.01" to as long as 0.5 inches, and having a non-aqueous content of between about 25% and about 35%. This stream, labeled as the $2^{nd}$ stream in FIGS. 1 and 2 is passed through a press that squeezes fluid from this stream and concentrates it to between about 40% to about 50% solids. The fluid removed from the $2^{nd}$ stream by the press contains water and some protein and oil. It is labeled as the $6^{th}$ stream, and is further processed to separate any oil and protein from it. The press may be a multidisc press or a screw press; however other press types also fall within the scope of this invention.

It is noted that the term "contains predominantly" refers to a content of more than 50% in the context of the present invention.

The low solids stream exiting the rotary screen contains predominantly water at between 95 percent and 99 percent, and oil and protein at between 1 to about 5 percent. It is labeled as the third stream in FIGS. 1 and 2. The third stream is sent to a Dissolved Air Floatation device (DAF) where it is separated into a fourth stream containing predominantly water at >99% and a fifth stream containing between about 75% to about 85% water and non-aqueous matter containing mostly protein and oil. Helping with the separation is polymer addition going into the pipe leading to the Dissolved Air Floatation device using the $2^{nd}$ and/or $3^{rd}$ inlets. If the pH of the third stream is lower than 5.5, between about 5 to about 25 ppm of a cationic acrylamide copolymer are added to the $2^{nd}$ inlet as shown in FIG. 1 which represents the schematic of the process for a DDGS stream having a pH<5.5. If the pH of the third stream is greater than 5.5, between about 5 to about 25 ppm of anionic acrylamide copolymer having a MW of between about 18 million to about 24 million is also added to the $3^{rd}$ inlet as shown in FIG. 2 which represent the schematic of the process for a DDGS stream having a pH>5.5.

The cationic acrylamide copolymer has a Molecular Weight of between about 8 million and about 19 million and between about 20 percent to about 40 percent charge.

The sixth stream may be combined with the fourth stream prior to entering the Dissolved Air Floatation device or combined with the effluent water in the fourth stream, depending on the oil and protein content of the sixth stream.

The $3^{rd}$ inlet is set about 15 seconds below the second inlet calculated based on the average volumetric flow rate through the pipe.

Next, the fifth stream is passed through either a multidisc press or a screw press that separates out of the fifth stream a low moisture (<30%) stream labeled as the seventh stream and a high moisture stream (>40%) labeled as the $12^{th}$ stream in FIGS. 1 and 2. The $12^{th}$ stream is passed through a vacuum drum to reduce the moisture content of the $12^{th}$ stream to between about 20 percent and about 30 percent. To aid in the water removal, about 5 to about 25 ppm of anionic acrylamide copolymer having a MW of between about 18 to about 24 million are added to the vacuum drum. The water removed from the vacuum drum is combined with the fourth stream and the combined water stream is treated with between about 5 to about 25 ppm of anionic acrylamide copolymer having a MW of between about 18 million to about 24 million in order to reduce the COD and BOD of the stream to dischargeable levels. The lower moisture stream exiting the vacuum drum is labeled as the $13^{th}$ stream.

The seventh stream is passed through a dryer where most of the moisture is removed leaving a cake of protein and oil having relatively large material chunks generally from about 0.1 inches to about 0.3 inches. This cake is labeled as the eighth stream. Also entering the dryer is the $13^{th}$ stream where it combines with the seventh stream.

The eighth stream is passed through a hammermill that reduces the particle sizes to generally less than 0.1" thereby generating a ninth stream. The ninth stream exiting the hammermill is pressed to separate out a stream that is predominantly oil ($10^{th}$ stream) from the cake and leaving the cake with a predominantly protein content ($11^{th}$ stream). The predominantly oil stream is about 97% pure. The press may be a heated oil press or another type of press suitable for this step. Water vapor in a temperature range of between 60° C. and about 88° C. may optionally be injected prior to the dryer to preheat the seventh stream and increasing moisture uniformity in the stream. The tenth stream may further be filtered and any residual protein precipitated out with the aid of between about 5 ppm to about 25 ppm of a cationic polyamine having a 50% charge and a MW of about 800,000 to bring the purity of the tenth stream to around 99%.

The following represents the important characteristics of the polymers used in the process.

Polyamines

Molecular weight between 10,000 and 1,000,000.

Liquid form with 40 to 50% concentration.

Cationic site on the main chain.

Viscosity at 50% concentration of between 40 and 20,000 centipoises.

Any polyamine having two $H_2N$ groups may be used in this application. An example may be 1,3-diaminopropane.

Cationic Acrylamide Copolymers

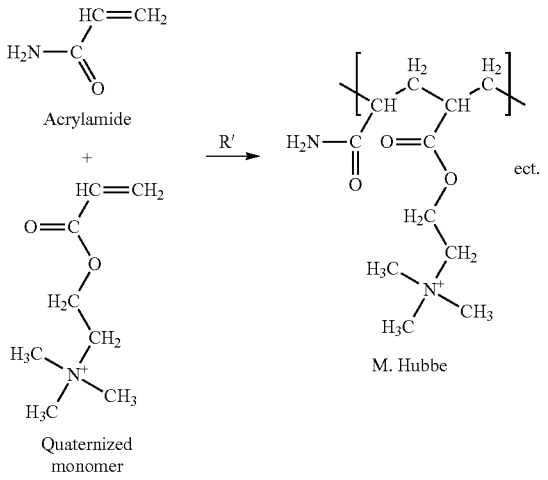

Sodium or Potassium Anionic Acrylate Acrylamide Copolymer.

This polymer may be made from the reaction between an acrylamide monomer and an acrylic acid monomer as shown below.

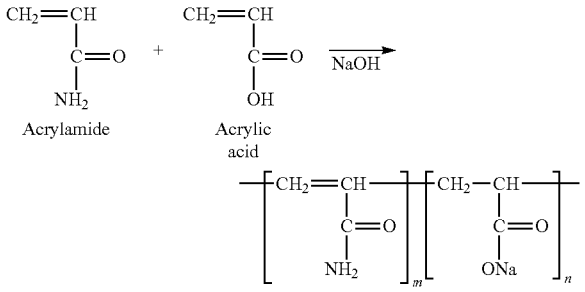

The anionicity of these copolymers can vary between 0% and 100% depending on the ratio of the monomers involved. The anionic copolymers used in the process of the present invention may have a molecular weight ranging between about 3 million to about 30 million, and a viscosity at a concentration of 5 g/l ranging from about 200 centipoises to about 2800 centipoises. The preferred pH range for making these copolymers is from 4.5 to 9. It is also noted that potassium may be substituted for the sodium as the base in the Acrylate Acrylamide copolymer.

It should be understood, of course, that the foregoing relates to exemplary embodiments of the invention and that modifications may be made without departing from the spirit and scope of the invention.

I claim:

1. A multi-stage substantially continuous process for separating a source stream *comprising dried distillers grain with solubles,* said source stream intermixedly containing fibers, water, protein and oil, said process being configured for separating the source stream into streams each containing predominantly one component, [said source stream containing dried distillers grains with solubles,] said process comprising the stages of:

(*a*) providing a source stream comprising [dried distillers grain with solubles, said dried distillers grain stream containing] water, oil, protein and fibers;

(*b*) separating said source stream into [a second stream and a third stream, said second stream having] a *first* non-aqueous portion containing predominantly fibers, [said third stream having] *and* a *second* non-aqueous portion containing predominantly a mixture of oil and protein[, separating a fourth stream and a fifth stream from said third stream, said fourth stream containing about 99 percent water and said fifth stream containing between about 15 percent to about 25 percent oil and protein,]*;*

(*c*) [wherein separating the fourth stream and the fifth stream from said third stream is accomplished by] passing said [third stream] *second non-aqueous portion* through a [second] chemical additive pipe having a [second] chemical addition inlet [and a third chemical addition inlet,] said [second] chemical additive pipe leading toward a [D]*d*issolved [A]*a*ir [F]*f*loatation device[, said third chemical addition configured to occur about 15 seconds after the second chemical addition based on an average volumetric flow rate through the pipe; adding between about 5 to about 25 ppm of a cationic acrylamide copolymer to the second chemical addition inlet; and feeding said third stream into the a Dissolved Air Floatation device wherein actions of said Dissolved Air Floatation device separate said third stream into the fourth stream and the fifth stream; and]*;*

(*d*) *adding about 5 to about 25 ppm of a cationic acrylamide copolymer to the second non-aqueous portion at the chemical addition inlet of the chemical additive pipe, so as to form a mixture of the cationic acrylamide copolymer and the second non-aqueous portion, the chemical additive pipe having a second chemical addition inlet and a third chemical addition inlet wherein a third chemical addition is configured to occur about 15 seconds after a second chemical addition based on an average volumetric flow rate through the pipe;*

(*e*) *separating said mixture of* (*d*) *into a predominantly water fraction and a non-aqueous fraction including oil, protein and water in the dissolved air flotation device, said predominantly water fraction containing about 99 percent water, said non-aqueous fraction containing between about 15 percent and about 25 percent oil and protein; and*

(*f*) separating from the [fifth stream a stream containing] *non-aqueous fraction of step* (*e*) *a* predominantly oil *fraction* and a [stream comprising] predominantly protein [through the steps of drying, size reduction, and pressing out the oil] *fraction,*

*wherein separating the source stream into the first non-aqueous portion and the second non-aqueous portion comprises: adding 5 to about 25 ppm of cationic polyamine to the source stream: separating the first non-aqueous portion and the second non-aqueous portion from said source stream with a rotary screen and wherein step* (*e*) *is accomplished by the steps of:*

*removing water from the non-aqueous fraction to achieve about 90 percent to about 95% solids content in the non-aqueous fraction, said water removal being accomplished by a pressing step, a vacuuming step and a drying step, said water removal step generating a dried cake containing predominantly oil and protein having particles;*

*reducing a particle size of the dried cake by passing the dried cake through a hammermill to generate a fragmented dried cake said fragmented dried cake containing predominantly oil and protein particles; and*

*passing the fragmented dried cake through a heated oil press to generate a dried fraction containing predominantly oil and a dried fraction containing predominantly protein.*

[2. The process of claim 1, wherein separating the source stream into the second stream and the third stream is accomplished by:

passing said source stream through a first chemical additive pipe having a first chemical addition inlet, said first chemical additive pipe leading toward a rotary screen;

adding between about 5 to about 25 ppm of cationic polyamine to the first stream at said first chemical addition inlet; and separating the second stream and the third stream from said source stream in the rotary screen.]

[3. The process of claim 1 wherein separating the fifth stream a stream containing predominantly oil and a stream comprising predominantly protein is accomplished by the steps of:

removing water from the fifth stream to achieve between about 90 percent and about 95% solids, said water removal being accomplished by a pressing step, a vacuuming step and a drying step, said water removal step generating an eighth stream, said eighth stream constituting of a dried cake containing predominantly oil and protein having a particles ranging in size between about 0.2 inches to about 0.5 inches;

reducing the particle size of the eighth stream by passing said eighth stream through a hammermill to generate a ninth stream, said ninth stream constituting of a dried cake containing predominantly oil and protein having particles ranging in size from between about 0.05 inches to about 0.2 inches; and separating the ninth stream into a tenth stream containing predominantly oil and an eleventh stream containing predominantly protein, said separating being accomplished by passing the ninth stream through a heated oil press.]

4. The process of claim [3] *1* further comprising passing the [tenth stream] *dried fraction containing predominantly oil* through a filter, while adding [between] about 5 to about 25 ppm of cationic polyamine to said filter [based on the average volumetric flow rate through the pipe], said polyamine addition resulting in precipitating any protein residual from said [tenth stream] *dried fraction containing predominantly oil*.

5. The process of claim [3 further comprising] *1 wherein the* pressing [the fifth stream, said pressing being] *step is* accomplished in either a multidisc press or a screw press, [wherein] *said* pressing [separates] *step separating* the [fifth stream] *non-aqueous fraction* into a [seventh stream] *first non-aqueous component* having a water content [between] *of* about 30 percent [and] *to* about 40 percent and a [twelfth stream containing] *second non-aqueous component having* a water content of above 40 percent, [said twelfth stream being passed] *and wherein the vacuuming step is accomplished by passing said second non-aqueous component* through a vacuum drum, said vacuum drum removing a water residue stream[, said water residue stream being combined with the fourth stream].

6. The process of claim 5, further comprising adding to the vacuum drum [between] about 5 to about 25 ppm of anionic acrylamide copolymer having a [MW] *molecular weight* of [between] about 18 million to about 24 million.

7. The process of claim [3] *1* wherein *the* drying [constitutes] *step comprises* passing the [seventh stream] *first non-aqueous component* through a dryer wherein water vapor in a temperature range of [between] about 60° C. and about 88° C. is injected prior to drying.

8. The process of claim 1, further comprising passing said [second stream] *first non-aqueous portion containing predominantly fibers* through a press to generate [a sixth stream] *an aqueous fraction*, said [sixth stream] *aqueous fraction* containing predominantly water, and combining the [sixth stream] *aqueous fraction* with the [third stream] *second non-aqueous portion* prior to [entering the Dissolved Air Floatation device] *step* (*e*).

9. The process of claim 1 further comprising treating the [fourth stream] *predominantly water fraction* with [between] about 5 to about 25 ppm of anionic acrylamide copolymer [to reduce] *thereby reducing* COD and BOD levels of said [fourth stream] *predominantly water fraction*.

10. The process of claim 1 further comprising *measuring the pH of said second non-aqueous portion and* adding [between] about 5 to about 25 ppm of [an] anionic acrylamide copolymer to said [third chemical addition inlet if] *second non-aqueous portion when* the pH of the [third stream] *second non-aqueous portion* is greater than 5.5.

11. The process of claim 1, wherein a charge of the cationic acrylamide copolymer is in a range of [between] about 20 percent [and] *to about* 40 percent.

*12. The process of claim 5, further comprising combining the water residue fraction with the predominantly water fraction.*

*13. The process of claim 1, wherein the predominantly water fraction contains at least 97% water by weight.*

*14. A process of separating components of waste material from ethanol production, the process comprising:*

*providing a source stream of waste material from ethanol production, the source stream comprising dried distillers grain with solubles and including water, fiber, protein, and oil components; and*

*separating the water, fiber, protein, and, oil components from the source stream into a predominantly water fraction, a predominantly fiber fraction, a predominantly protein fraction, and a predominantly oil fraction by:*

(*a*) *removing fiber components from the source stream to produce the predominantly fiber fraction and a low solids stream including water, protein, and oil;*

(*b*) *treating the low solids stream with a cationic acrylamide polymer to form a treated low solids stream, said treating the low solids stream with a cationic acrylamide polymer being accomplished through chemical addition to a pipe containing a second chemical addition inlet and a third chemical addition inlet wherein a third chemical addition is configured to occur about 15 seconds after a second chemical addition based on an average volumetric flow rate through the pipe;*

(*c*) *passing the treated low solids stream in* (*b*) *through a dissolved air flotation device that separates the treated low solids stream into the predominantly water fraction and a non-aqueous fraction including oil, protein and water, the predominantly water fraction containing about 99 percent water, the non-aqueous fraction containing about 15 percent to about 25 percent oil and protein;*

(*d*) *removing water from the non-aqueous fraction in* (*c*) *to form a predominantly protein and oil mixture fraction; and*

(*e*) *separating the predominantly protein and oil mixture fraction into the predominantly protein fraction and the predominantly oil fractions;*

*wherein removing fiber components from the source stream to produce the predominantly fiber fraction comprises:*

*adding about 5 to about 25 ppm of cationic polyamine to the source stream;*

*separating the predominantly fiber fraction and the low solids stream from said source stream with a rotary screen;*

*wherein separating the predominantly protein and oil mixture fraction into the predominantly protein fraction and the predominantly oil fraction comprises:*

*removing water from the non-aqueous fraction to achieve about 90 percent to about 95 percent solids content in the non-aqueous fraction, said water removal being accomplished by a pressing step, a vacuuming step and a drying step, said water removal step generating a dried cake containing predominantly oil and protein particles;*

*reducing a particle size of the dried cake by passing the dried cake through a hammermill to generate a fragmented dried cake, said fragmented dried cake containing predominantly oil and protein particles; and*

*passing the fragmented dried cake through a heated oil press to generate a dried fraction containing predominantly oil and a dried fraction containing predominantly protein.*

*15. The process of claim 14, further comprising passing the dried fraction containing predominantly oil through a filter, while adding about 5 to about 25 ppm of cationic polyamine to said filter, said polyamine addition resulting in precipitating any protein residual from said dried fraction containing predominantly oil.*

*16. The process of claim 14, wherein the pressing step is accomplished in either a multidisc press or a screw press, said pressing step separating the non-aqueous fraction into a first non-aqueous component having a water content of about 30 percent to about 40 percent and a second non-aqueous component having a water content of above 40 percent, and wherein the vacuuming step is accomplished by passing said second non-aqueous component through a vacuum drum, said vacuum drum removing a water residue fraction.*

*17. The process of claim 16, further comprising adding to the vacuum drum about 5 to about 25 ppm of anionic acrylamide copolymer.*

*18. The process of claim 16, further comprising combining the water residue fraction with the predominantly water fraction.*

*19. The process of claim 14, wherein the drying step comprises passing the first non-aqueous component through a dryer wherein water vapor in a temperature range of about 60° C. to about 88° C. is injected prior to drying.*

*20. The process of claim 14, further comprising: passing said predominantly fiber fraction through a press to generate an aqueous fraction, said aqueous fraction containing predominantly water; and combining the aqueous fraction with the low solids stream prior to step (c).*

*21. The process of claim 14, further comprising treating the predominantly water fraction with about 5 to about 25 ppm of anionic acrylamide copolymer, thereby reducing COD and BOD levels of said predominantly water fraction.*

*22. The process of claim 14, further comprising measuring a pH of the low solids stream and adding an anionic acrylamide copolymer to said low solids stream when the pH of the low solids stream is greater than 5.5.*

*23. The process of claim 14, wherein a charge of the cationic acrylamide copolymer is in a range of between about 20 percent and 40 percent.*

*24. The process of claim 14, wherein the predominantly water fraction contains at least 97% water by weight.*

* * * * *